United States Patent [19]

Pawloski et al.

[11] Patent Number: 4,668,710
[45] Date of Patent: May 26, 1987

[54] TRIHALOVINYL POLYOL ETHERS

[75] Inventors: Chester E. Pawloski, Bay City; William J. Kruper, Jr., Sanford, both of Mich.

[73] Assignee: The Dow Chemical Company, Midland, Mich.

[21] Appl. No.: 812,881

[22] Filed: Dec. 23, 1985

[51] Int. Cl.$^4$ ............................................. C08G 18/14
[52] U.S. Cl. ..................... 521/171; 252/182; 528/70; 528/75; 560/25; 560/26; 560/115; 560/158; 560/197; 570/125; 570/126; 570/135; 570/136; 570/137; 570/138; 570/189
[58] Field of Search ................... 521/171; 528/70, 75; 252/182; 560/25, 26, 115, 158, 197; 570/125, 126, 135, 136, 137, 138, 189

[56] References Cited

U.S. PATENT DOCUMENTS

| | | | |
|---|---|---|---|
| Re. 24,514 | 8/1958 | Hoppe et al. | 260/2.5 |
| 1,922,459 | 8/1933 | Schmidt et al. | 260/106 |
| 2,871,219 | 1/1959 | Baggett et al. | 260/45.95 |
| 2,891,073 | 6/1959 | Smith | 260/340.2 |
| 3,058,921 | 10/1962 | Pannell | 260/2 |
| 3,215,652 | 11/1965 | Kaplan | 260/2.5 |
| 3,402,169 | 9/1968 | Jackson | 260/106 |
| 3,483,263 | 12/1969 | Schlichting et al. | 260/633 |
| 3,755,212 | 8/1973 | Dunlap et al. | 260/2.5 |
| 3,821,130 | 6/1974 | Barron et al. | 260/2.5 |
| 3,849,146 | 11/1974 | Walters et al. | 96/107 |
| 3,928,299 | 12/1975 | Rosenkranz et al. | 260/89.5 |
| 4,052,349 | 10/1977 | Turley et al. | 260/17.2 |
| 4,083,825 | 4/1978 | Albright et al. | 260/963 |
| 4,298,709 | 11/1981 | Ginter | 521/169 |
| 4,365,026 | 12/1982 | Pawloski et al. | 521/168 |

FOREIGN PATENT DOCUMENTS 898306 6/1962 United Kingdom .

OTHER PUBLICATIONS

Rebek et al., *J. Org. Chem.*, 43, 180–181 (1978).
Bach et al., *J. Org., Chem.*, 44, 2569–2571 (1979).
Matsumura et al., *Tet. Letts.*, 2029–2032 (1970).
Carlson et al., *J. Org. Chem.*, 36, 2319–2324 (1971).
Guilmet et al., *Nouv. J. Chem.*, 6, 511–513 (1982).
Mansuy et al., *J. Chem. Soc. Chem. Commun.*, 253–254 (1983).
Groves et al., *J. Am. Chem. Soc.*, 101, 1032–1033, 7613–7615 (1979).
Groves et al., *J. Am. Chem. Soc.*, 102, 6375–6377 (1980).
Venturello et al., *J. Org. Chem.*, 48, 3831–3833 (1983).
Kirk-Othmer Encyclopedia of Chemical Technology, "Foamed Plastics", vol. 9, pp. 853—854 (1966).
Sanders et al., *Polyurethanes, Chemistry and Technology*, vols. I and II, Interscience Publishers, 1963.
Woller, *J. Am. Chem. Soc.*, 49, 3181 (1947).
Encyclopedia of Chemical Technology, 18, 633–645; 19, 249–250, Interscience Publishers, Inc. (1982).
Shick, M. J., *Nonionic Surfactants*, Marcel Dekker, Inc. NY (1967).
ANSI/ASTM D-2863-2877, California Technical Bulletin 117 (1980).
ASTM E-84.

*Primary Examiner*—Maurice J. Welsh

[57] ABSTRACT

Included are trihalovinyl polyol ethers. The compositions have pendant 1,2,2-trihaloethenyl moieties. The compositions may be low viscosity oils or highly polymeric such as incorporated with a urethane or other polymers. One of the uses of the compositions is as flame retardants which may have high thermal stability and scorch resistance.

22 Claims, No Drawings

TRIHALOVINYL POLYOL ETHERS

FIELD OF THE INVENTION

The invention relates to halogenated polyol ethers. These compounds are preferably used in flame-retardant applications, for example, in the production of flame-retardant polyurethane and polyester compositions.

BACKGROUND OF THE INVENTION

Halogenated polyol ethers are known. They are generally useful as flame retardants. Certain halogenated polyol ethers having pendant polyhaloaliphatic moieties are known. They, too, are generally useful, for example, as flame retardants and as adhesives.

For example, Jackson, U.S. Pat. No. 3,402,169 (1968) (incorporated herein by reference), discloses certain cogeneric polyhalogenated polyol ethers characterized by pendant $C_{1-2}$ haloalkyl groups with at least two, preferably three, halogens attached to the terminal carbon. The flame-retardant products range in physical state from viscous liquids to glassy, brittle solids.

Turley et al., U.S. Pat. No. 4,052,349 (1977) (incorporated herein by reference), disclose an epoxy resin which incorporates a polyol with at least one 2,2-dichloroethenyl group in the polyol chain. The pendant dichlorovinyl group enhances adhesive bonding properties of the resin, and the resin has reduced combustibility characteristics in comparison to nonhalogenated epoxies.

What is lacking and what is needed are polyhalogenated polyol ethers with good physical properties and with high flame-retardant capability, thermal stability and scorch resistance.

SUMMARY OF THE INVENTION

The invention comprises trihalovinyl polyol ethers. The trihalovinyl polyol ethers contain the 1-(1,2,2-trihaloethenyl)-1,2,2-tri-substituted ethoxy moiety of which the 1,2,2-trihaloethenyl moiety is a pendant moiety.

Another aspect of the invention comprises more highly polymerized trihalovinyl polyol ether copolymer compositions. Comonomers are any other monomer compositions copolymerized with the trihalovinyl polyol ethers.

The compositions of the invention are useful in flame-retardant applications and may be used in adhesive applications. The compositions preferably have high flame-retardant capability, thermal stability and scorch resistance. The compositions preferably also have low viscosity.

The composition contains the novel 1-(1,2,2-trihaloethenyl)-1,2,2-tri-substituted ethoxy moiety. The surprising properties of the composition of the invention may often result from the incorporation of this moiety.

DETAILED DESCRIPTION OF ILLUSTRATIVE EMBODIMENTS

The invention comprises trihalovinyl polyol ethers. The trihalovinyl polyol ethers contain the 1-(1,2,2-trihaloethenyl)-1,2,2-tri-substituted ethoxy moiety of which the 1,2,2-trihaloethenyl moiety is a pendant moiety.

One preferred aspect of the invention includes trihalovinyl polyol ether compositions of the general formula:

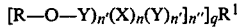

wherein

R is independently at each occurrence hydrogen, $C_{1-20}$ hydrocarbyl, $C_{1-20}$ halocarbyl, $C_{1-20}$ halogenated hydrocarbyl, $C_{1-20}$ hydroxylated hydrocarbyl, $C_{1-20}$ hydroxylated halocarbyl, or $C_{1-20}$ halogenated-hydroxylated hydrocarbyl, each of which may additionally contain other ether functionality and $C_{1-20}$ attached organic or attached inorganic moiety;

$R^1$ is independent at each occurrence hydrogen, $C_{1-20}$ attached organic or attached inorganic moiety;

X is independently at each occurrence 1-(1,2,2-trihaloethenyl)-1,2,2-tri-substituted ethoxy;

Y is independently at each occurrence 1,1,2,2-tetra-substituted ethoxy;

n is independently at each occurrence an integer from one to about 20;

n' is independently at each occurrence an integer from zero to about 20;

n'' is independently at each occurrence an integer from one to about 20; and q is independently at each occurrence an integer from one to three.

The trihalovinyl polyol ethers are preferably the aspect that includes the compositions of said formula $[R(-O-(-Y)_{\overline{n}}(X)_{\overline{n}}(Y)_{\overline{n'}}]_q R^1$. Compositions of the formula $R(-O-(-Y)_{\overline{n}}(X)_{\overline{n}}(Y)_{\overline{n'}}]R^1$ are preferred (i.e., q is one).

R may be a $C_{1-20}$ hydrocarbyl moiety. $C_{1-20}$ hydrocarbyl means a moiety that contains from one to about 20 carbons, at least one hydrogen and no other elements. The $C_{1-20}$ hydrocarbyl moiety may be aromatic or aliphatic, which may be unsaturated or saturated and may be straight-chained, branched, alicyclic or combinations thereof, or the $C_{1-20}$ hydrocarbyl moiety may be a combination of aromatic and aliphatic moieties.

R may be a $C_{1-20}$ hydrocarbyl moiety. Halocarbyl means that halogens are independently substituted for all the hydrogens of a hydrocarbyl moiety.

Halogens herein include fluorine, chlorine and bromine. Preferred herein are chlorine and bromine. There may be more preferred halogens for particular moieties, which are noted herein.

R may be $C_{1-20}$ halogenated hydrocarbyl. Halogenated hydrocarbyl means that a halogen has been substituted for a hydrogen in the $C_{1-20}$ moiety, but at least one hydrogen is bonded to a carbon of the moiety.

R may be $C_{1-20}$ hydroxylated hydrocarbyl. Hydroxylated hydrocarbyl means that a hydroxyl group has been substituted for a hydrogen in the $C_{1-20}$ moiety, but at least one hydrogen is bonded to a carbon of the moiety.

R may be $C_{1-20}$ hydroxylated halocarbyl. Hydroxylated halocarbyl means that hydroxyl and halogen has been substituted for all the hydrogens of a hydrocarbyl moiety.

R may be $C_{1-20}$ halogenated-hydroxylated hydrocarbyl. Halogenated-hydroxylated hydrocarbyl means that together hydroxyl and independent halogen have been substituted for at least two hydrogens in the $C_{1-20}$ moiety, but at least one hydrogen is bonded to a carbon of the moiety.

R may additionally contain other ether functionality. The ether functionality may be part of a straight, branched or cyclic moiety. More than one such ether functionality may be present.

R may additionally contain a $C_{1-20}$ attached organic or attached inorganic moiety. The attached moieties are attached by reactions with the functionality present within the R moiety. For example, if R has an unsaturated aliphatic bond, it may add $H_2SO_4$, especially to a double bond; it may add aqueous mercuric acetate, especially to a double bond; it may form heavy metal or alkali metal acetylides if a reactive triple bond is present. If R has hydroxyl functionality, advantage of this functionality may be taken, for example, by active metal (e.g., Na, K, Mg, Al, etc.) substitution for the hydroxyl hydrogen. If R has a halogen, especially a more labile halogen, than on other parts of the composition, advantage of this may be taken by reaction, for example, with cyanide, carbonyl compounds, amines, thiols, and the like. Other ether functionality may be introduced in this manner by Williamson synthesis. Conditions are such that the additions to R of the trihalovinyl polyol ether are carried out.

Preferably, R is independently at each occurrence hydrogen, $C_{1-10}$ hydrocarbyl, $C_{1-10}$ halogenated-monohydroxylated hydrocarbyl, $C_{1-10}$ halogenated hydrocarbyl, $C_{1-6}$ mono-hydroxylated hydrocarbyl or $C_{1-6}$ halocarbyl. More preferably, R is hydrogen or is an aromatic, alkenyl, cycloalkenyl, alkyl, cycloalkyl moiety or combination thereof variant of said preferred $C_{1-10}$ and $C_{1-6}$ R moieties. Most preferably, R is hydrogen or a $C_{1-6}$ variant of said more preferred $C_{1-10}$ R moieties or is the said more preferred $R_{1-6}$ R moieties. R may contain dealkylatable alkyl (e.g., tertiary carbon) ether.

Especially preferred are neocarbyl R moieties. Neocarbyl R moieties include R moieties of the formula:

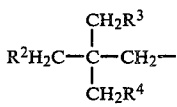

wherein
$R^2$ is independently at each occurrence hydroxyl or halogen, more especially bromine; and
$R^3$ and $R^4$ are independently at each occurrence hydrogen or halogen, more especially bromine, and preferably $R^3$ and $R^4$ are each the same.

The most especially preferred neocarbyl R moieties are 2,2-bis(bromomethyl)-3-hydroxypropyl and 3-bromo-2,2-bis(bromomethyl)propyl.

R is preferably a remnant of a hydroxy-containing compound. Preferably, the hydroxyl functionality has been reacted to form an adduct with the oxirane precursors to X and Y.

$R^1$ may be a $C_{1-20}$ attached organic or attached inorganic moiety. The attached $R^1$ moieties are attached by reaction with the 1-oxy functionality of Y, preferably as a Y-OH functionality or Y-O$R^1$ functionality, when $R^1$ is dealkylatable alkyl (e.g., tertiary carbon, such as may be found when Y is reacted with a compound such as t-butylglycidyl ether, which may later be dealkylated to hydroxyl functionality as desired by reaction with an acid such as $H_3PO_4$). For example, active metals may attach; esters or thioesters may be formed; if the Y-OH functionality is a primary hydroxyl functionality, oxidation with $K_2Cr_2O_7$ or $KMnO_4$ may yield aldehyde or carboxylic acid functionality; other organic groups may attach to the oxy functionality by the Williamson ether synthesis. Conditions are such that the $C_{1-20}$ or inorganic $R^1$ moiety is attached.

Preferably, $R^1$ is hydrogen, $C_{1-10}$ hydrocarbyl or $Na^+$ or $K^+$. More preferably, $R^1$ is hydrogen or dealkylatable $C_{1-10}$ alkyl. Most preferably, $R^1$ is hydrogen, especially when present after dealkylation of the dealkylatable $C_{1-10}$ alkyls.

X is independently each occurrence 1-(1,2,2-trihaloethenyl)-1,2,2-tri-substituted ethoxy. X includes moieties of the formula:

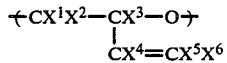

wherein
$X^1$, $X_2$ and $X^3$ are each independently hydrogen, $C_{6-20}$ aryl, $C_{7-20}$ arylalkyl or alkylaryl, or $C_{1-20}$ alkyl; and
$X^4$, $X^5$ and $X^6$ are each independently halogen.

The 1-(1,2,2-trihaloethenyl)-1,2,2-tri-substituted ethoxy moieties are preferably remnants of the corresponding (1,2,2-trihaloethenyl)oxiranes. The (1,2,2-trihaloethenyl)oxiranes are $\beta,\gamma,\gamma$-trihalo-$\beta,\gamma$-unsaturated-$\alpha$-oxiranes, wherein the common (i.e., Greek) nomenclature is assigned based on a four-carbon core: $\beta$ relates to the number three carbon; $\gamma$ relates to the number four carbon; and the $\alpha$-oxirane ring involves the number one and two carbons. The halo-functionality therein includes fluoro-, chloro- and bromo-functionality. The (1,2,2-trihaloethenyl)oxiranes may be substituted with up to three organic moieties other than hydrogen onto the number one and two carbons of the four-carbon core.

The (1,2,2-trihaloethenyl)oxiranes are preferably represented by the general formula:

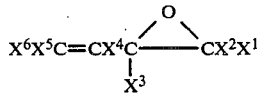

wherein
$X^1$, $X^2$ and $X^3$ are each independently hydrogen, $C_{6-10}$ aryl, $C_{7-20}$ arylalkyl or alkylaryl, or $C_{1-20}$ alkyl; and
$X^4$, $X^5$ and $X^6$ are each independently F (i.e., fluoro), Cl (i.e. chloro) or Br (i.e., bromo).

$C_{6-20}$ aryl indicates an aromatic hydrocarbon moiety of from 6 to about 20 carbons that does not have aliphatic side chains. Preferred aryl moieties include phenyl and naphthyl.

$C_{7-20}$ arylalkyl indicates an aromatic hydrocarbon moiety having straight or branched and/or cyclic alkyl and/or alkylaryl functionality attached to the aromatic ring. An aryl portion is bonded to the oxirane-carbon. The moiety is from 7 to about 20 carbons. Preferred arylalkyl moieties include o-, m- and/or p-tolyl and o-, m- and/or p-ethylphenyl.

$C_{7-20}$ alkylaryl indicates a straight or branched and/or cyclic alkyl hydrocarbon moiety having aryl and/or arylalkyl functionality attached. An alkyl portion is bonded to the oxirane-carbon. The moiety is from 7 to about 20 carbons. Preferred alkylaryl moieties include benzyl, o-, m- and/or p-methylbenzyl and o-, m- and/or p-ethylbenzyl.

$C_{1-20}$ alkyl indicates a straight or branched and/or cyclic saturated hydrocarbon moiety. The moiety is from 1 to about 20 carbons. More preferred alkyl moieties include methyl and ethyl, with methyl most preferred.

Preferred (1,2,2-trihaloethenyl)oxiranes include those wherein $X^1$, $X^2$ and $X^3$ are independently hydrogen or $C_{1-4}$ (i.e., from 1 to 4 carbons) alkyl. More preferred are those wherein $X^1$, $X^2$ and $X^3$ are independently hydrogen, methyl or ethyl. Most preferred are those wherein at least $X^2$ is hydrogen. It is especially preferred that each of $X^1$, $X^2$ and $X^3$ is hydrogen.

Preferred (1,2,2-trihaloethenyl)oxiranes are also those wherein $X^4$ and $X^6$ are independently F, Cl or Br, with $X^5$ being Cl or Br. More preferred are those wherein $X^4$, $X^5$ and $X^6$ are independently Cl or Br. Most preferred are (1,2,2-trichloroethenyl)oxiranes.

Thus, the most especially preferred of the (1,2,2-trihaloethenyl)oxiranes is (1,2,2-trichloroethenyl)-1,2-ethylene oxide.

The (1,2,2-trihaloethenyl)oxiranes can be prepared by epoxidation of corresponding 1,1,2-trihalo-1,3-dienes. Conditions are such that the (1,2,2-trihaloethenyl)oxiranes are produced.

Epoxidation is carried out with epoxidation agents which are a source of elemental oxygen. Preferably, the epoxidation is done with electrophilic epoxidation agents such as sodium hypochlorite, peroxides like hydrogen peroxide (Rebek et al., *J. Org. Chem.* 43, 180–181 (1978)), peroxycarbonic acids (Bach et al., *J. Org. Chem.*, 44, 2569–2571 (1979)), N-arylperoxycarbonic acids (Matsumura et al., *Tet. Letts.*, 2029–2032 (1970)) and peroximidic acids (Rebek et al., supra), the well-known meta-chloroperoxybenzoic acid or trifluoroperacetic acid if the 1,1,2-trihalo-1,3-diene is fluoro-substituted. A catalyst such as metalloporphorinates of Mn, Mn (V), Cr (V), and Fe (III), especially in conjunction with sodium hypochlorite (see, Carlson et al., *J. Org. Chem.*, 36, 2319–2324 (1971); Guilmet et al., *Nouv. J. Chim.*, 6, 511–513 (1982); Mansuy et al., *J. Chem. Soc. Chem. Commun.*, 253–254 (1983); Groves et al., *J. Am. Chem. Soc.*, 101, 1032–1033, 7613–7615 (1979); Groves et al., *J. Am. Chem. Soc.*, 102, 6375–6377 (1980)), and $Na_2WO_4 \cdot 2H_2O$, especially in conjunction with dilute hydrogen peroxide (see, Venturello et al., *J. Org. Chem.*, 48, 3831–3833 (1983)), may be advantageous. (Each of the foregoing articles is incorporated herein by reference). The use of phase-transfer catalysts such as organic-substituted ammonium salts may be advantageous in multi-phase reaction systems. (See Venturello et al., supra). Preferred are tert-alkylamine halides. Preferably therein, the molar ratio of the 1,1,2-trihalo-1,3-diene to epoxidation agent is from about 3:4 to about 4:3, and the reaction is carried out in an inert solvent under an inert atmosphere.

Inert solvents include, for example, liquid alkanes and saturated halocarbons. Preferred are $C_{1-2}$ saturated halocarbons, most preferably $C_{1-2}$ saturated chlorocarbons, such as carbon tetrachloride, methylene chloride and ethylene dichloride. Inert atmospheres include, for example, argon and nitrogen blankets.

Preferably, the temperature of reaction is from about 30° C. to about 50° C. Higher temperatures may enhance unwanted polymerizations. Pressures are preferably atmospheric.

Time of reaction may vary considerably. Times of reaction of from about 2 to 72 hours are preferred. A more preferable upper limit is about 40 hours. The preparation of fluoro-substituted (1,2,2-trihaloethenyl)oxiranes typically requires more time. Longer times may enhance unwanted polymerizations.

The (1,2,2-trihaloethenyl)oxiranes may be used without separation from the reaction mixture or may be separated and purified. Separation of unreacted epoxidation agent from the reaction mixture by extraction with aqueous alkali metal bisulfites and hydroxides is a preferred method of preliminary purification. Preferably, the (1,2,2-trihaloethenyl)oxiranes are then dried using a drying agent. Drying agents may include molecular sieves and anhydrous inorganic chemicals such as magnesium sulfate. Further purification may be by other known methods, including chromatographic methods and distillation. Distillation may be used to remove a volatile solvent from the reaction mixture as desired. Distillation may also be used to separate the (1,2,2-trihaloethenyl)oxiranes, as desired and appropriate. Distillation under vacuum is preferred.

The corresponding 1,1,2-trihalo-1,3-dienes may be made by methods known in the art such as by the dehydration of trihalovinyl alcohols, as taught by Schlichting et al., U.S. Pat. No. 3,483,263 (1969) (incorporated herein by reference). A preferred method of incorporating carbonaceous $R^3$ functionality is by reaction of the corresponding Grignard reagent with the corresponding trihalovinylalcohols.

Thus, X is most preferably 1-(1,2,2-trichloroethenyl)ethoxy.

Y is independently each occurrence 1,1,2,2-tetra-substituted ethoxy. Y includes moieties of the formula:

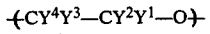

wherein $Y^1$, $Y^2$, $Y^3$ and $Y^4$ are each independently R; the oxy moiety being on the number one carbon of the Y moiety. The 1,1,2,2-tetra-substituted ethoxy moieties are preferably remnants of the corresponding 1,1,2,2-tetra-substituted oxiranes which are known or can be prepared by known methods. A preferred method is the epoxidation of the corresponding 1,1,2,2-tetra-substituted ethylene by electrophilic epoxidation agents such as m-chloroperoxy benzoic acid, trifluoro peracetic acid (for F groups) and $H_2O_2$ in conjunction with $NaWO_4 2H_2O$.

Especially preferred are Y moieties wherein $Y^1$, $Y^2$, $Y^3$ and $Y^4$ are independently each occurrence hydrogen, halogen or $C_{1-4}$ alkyl, haloalkyl, hydroxylalkyl, $C_{2-4}$ alkenyl or mono- and dihaloalkenyl. Most especially preferred Y moieties are independently each occurrence 1-methoxyethoxy, 1-chloromethylethoxy, 1-methylethoxy and ethoxy.

More preferably, n is independently each occurrence from one to about 15, most preferably from one to 5. More preferably, each n' is independently each occurrence from one to about 15. Most preferably, the sum of each n' is about 20 or less. More preferably, n'' is from one to about 5, most preferably from one to 4.

The preferred trihalovinyl polyol ether compositions which include compositions inclusive of said formula $[R\text{-}[O\text{-}(Y)_{\overline{n}}(X)_{\overline{n}}(Y)_{\overline{n}}]n''\text{-}]_{\overline{q}}R^1$ are prepared by contacting the hydroxy compounds with the oxiranes corresponding to the oxiranes remnants X and Y under conditions such that the trihalovinyl polyol ethers are prepared. Additional moieties may be reacted, especially as noted herein. The compositions are typically cogeneric mixtures.

A preferred method of preparing the compositions inclusive of said formula $[R\text{---}O\text{---}Y)_{n'}(X)_n(Y)_{n'}]_{n''}]_qR^1$ is by the general method taught by Jackson, U.S. Pat. No. 3,402,169 (1968), columns 2-13. Preferably, a catalyst is present. Preferred catalysts are Lewis acids such as boron trifluoride ethyl ether (i.e., BF$_3$-etherate). Preferably, an inert solvent is present. Preferred solvents are halogenated alkanes such as chloroform and methylene chloride. Preferably, the reaction is quenched by the addition of base or lowering the temperature, more preferably by base addition such as by adding 5 percent NaOH (aqueous). The following preferred sequence is illustrative:

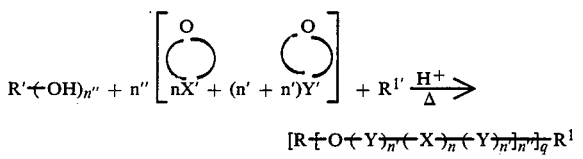

$$[R\text{+}O\text{+}Y)_{\overline{n'}}(X)_{\overline{n}}(Y)_{\overline{n'}}]_{\overline{n''}}]_qR^1$$

wherein the primes (i.e., ') include corresponding residues of precursors to R, R$^1$, X and Y. Preferred amounts of reactants are the stoichiometric amounts of each precursor to R, X and Y, and R$^1$ as desired.

Preferred temperatures overall are from about 0° C. to about 150° C. More preferred temperatures are from about 25° C. to about 120° C. Temperatures of the preparation of the trihalovinyl polyol ethers of the formula $[R\text{+}O\text{+}Y)_{\overline{n'}}(X)_{\overline{n}}(Y)_{\overline{n'}}]_{\overline{n''}}]_qR^1$ from the precursors to R, R$^1$, X and Y in the formula are typically in the lower portions of the preferred ranges, preferably such as about 100° C. or below, more preferably about 70° C. or below and most preferably about 40° C. or below. Temperatures of any subsequent steps such as distillations or removal of solvent which are desired are typically in the higher portions of the preferred ranges, preferably such as about 40° C. or above, more preferably about 70° C. or above and most preferably about 100° C. or above.

It may be advantageous to react the precursors in sequence to obtain the desired composition. For example, one R precursor and two X precursors may be reacted, and one Y precursor is then reacted with the nominal R(-X-)$_2$ adduct to prepare a nominal R(-X-)$_2$(Y)- adduct. The word "nominal" is used to indicate that the sequentially reacted compositions are also typically cogeneric.

As a flame retardant, the compositions inclusive of said formula $[R\text{+}O\text{+}Y)_{\overline{n'}}(X)_{\overline{n}}(Y)_{\overline{n'}}]_{\overline{n''}}]_qR^1$ are added in any amount which is effective to lower the combustibility of the otherwise more flammable material to any degree. By flame-retardant is meant that the trihalovinyl polyol ether when incorporated in the more flammable material reduces the propensity of the more flammable material (e.g., polyurethane) to propagate combustion after the removal of a small scale ignition source such as a lit Bunsen burner.

Any amount of the trihalovinyl polyol ethers which is flame retardant is suitable for this invention. Preferably, flame-retardant amounts of are between about 5 and 100 parts by weight of the composition, for example, of polyahl of a polyurethane, most preferably between about 10 and 50 parts by weight.

One preferred method to measure this flame-retardant capability is an oxygen index (i.e., limiting oxygen index) measured by the oxygen demand test of ANSI/ASTM D-2863-77 (ASTM American National Standard) wherein the minimum concentration of oxygen in a mixture of dry O$_2$ and dry N$_2$ flowing upward, needed to cause combustion in a standard test column that will just support combustion under equilibrium conditions of candle-like burning is measured. Other conditions of the ANSI/ASTM D-2863-77 oxygen demand test include those set out in the ASTM American National Standard test (incorporated herein by reference).

Preferably, for ten appropriate A through D type (as in the D-2863-77 standard) specimens with the flame-retardant composition, the average limiting oxygen index (i.e., average LOI) is raised 10 percent or more, more preferably 20 percent or more and most preferably 30 percent or more, when measured either by time until extinguishing of the flame or distance of the burned specimen according to ASTM D-2863-77, when compared to ten otherwise comparable specimens without the flame-retardant composition. It is also preferred that the average LOI of ten appropriate A through D type specimens is raised to above 21, more preferably to about 25 or above and most preferably, to about 30 or above. For example, specimens of a styrenic polymer resin such as resinous polystyrene and poly(acrylonitrile-butadiene-styrene) may have an average LOI of 18 before the incorporation of flame retardant and an average LOI of 25 afterward, which is a concurrent increase in average LOI of 39 percent; specimens of an alkylene polymer resin such as resinous polyethylene or polypropylene may have an average LOI of 17 before and 27 afterward; specimens of a polymer resin such as a polycarbonate may have an average LOI of 25 before and 32 afterward.

When incorporated into a rigid polyurethane foam, such as in insulating foam, preferred measures include the Steiner tunnel test of ASTM E-84 or the equivalent such as Underwriter's Laboratories (i.e., UL) 723. It is preferred that the rigid foam pass the E-84 test or equivalent with a Class III rating or better, more preferably a Class II rating or better. It may be desired to incorporate into the flame-retardant composition an amount effective to secure a Class I rating. Other tests such as the German DIN-4012-B2 test or its Swiss counterpart may be used.

When incorporated into a flexible polyurethane foam as a flame retardant, a preferred measure of the flame-retardant composition is the California 117 test such as in California Technical Bulletin 117, State of California, Department of Consumer Affairs, Bureau of Home Furnishings, North Highlands, Calif. (January, 1980) (incorporated herein by reference). It is preferred that the California 117 test is passed by the flame-retardant flexible foam composition.

Preferably, the compositions inclusive of said formula $[R\text{+}O\text{+}Y)_{\overline{n'}}(X)_{\overline{n}}(Y)_{\overline{n'}}]_{\overline{n''}}]_qR^1$ have high thermal stability. One preferred method to measure this is by thermogravimetric analysis (i.e., TGA), where the sample tested is continuously monitored for weight loss as its temperature is progressively increased in an oven with a nitrogen atmosphere. Preferably, the progressive temperature increase is at a rate of 20° C. per minute from an initial temperature of 20° C. with the sample size initially between 0.010 g and 0.020 g. Under these preferred test conditions, TGA's preferably have at 50 percent weight loss of sample (i.e., TGA$_{50}$) a temperature of about 200° C. or above, more preferably about 250° C. or above and most preferably about 280° C. or above. It is especially preferred that the TGA$_{50}$ is about 300° C. or above, more especially about 320° C. or above and most especially about 360° C. or above.

Preferably, the flame-retardant agent or resulting more highly polymerized flame-retardant compositions show high scorch resistance. By scorch resistance is meant resistance to discoloration, especially when added to or copolymerized with other structural polymer monomers, most especially in polyurethanes and polyesters. Preferably, the composition shows by the Gardner Colorimeter test a ΔE in National Bureau of Standards (i.e., NBS) units of about 10 or below, most preferably about 6 or below and most preferably about 4 or below in comparison to the material without the composition and otherwise the same (i.e., a control sample). See Albright et al., U.S. Pat. No. 4,083,825 (1978) (incorporated herein by reference) at column 8, line 58 to column 11, line 23.

Preferably, the compositions inclusive of the formula $[R\{-O-(Y)_{\overline{m}}(X)_{\overline{n}}(Y)_{\overline{m}}]_{\overline{n}}]_q R^1$ are liquids at room temperature and have low viscosity. One preferred method to measure the viscosity is by Brookfield viscometer, which is measured at 25° C. The Brookfield viscosity is measured with a number 6 spindle submersed with sample in a vessel of a width at least 125 percent the diameter of the spindle. The number of spindle revolutions per minute is 100. Preferred values of the Brookfield viscosity are, in units of centipoise (cps), about 200,000 cps or below, more preferably about 20,000 cps or below and most preferably about 5,000 cps or below. It is especially preferred that the viscosity is about 2,000 cps or below, more especially about 500 cps or below.

To obtain the especially preferred viscosities, the reaction may be stopped at low molecular weight composition. Preferably, the especially low viscosity compositions are formed in stoichiometric molar ratios of R:X:Y of from 1:1:2 to 1:1:3, more preferably about 1:1:2. Also preferably therein, Y is a two or three carbon moiety, more preferably three. Examples of preferred Y precursors therein include ethylene oxide, propylene oxide, epichlorohydrin and epibromohydrin.

Also, dealkylatable $R^1$ groups attached and subsequently dealkylated may provide low viscosity trihalovinyl polyol ethers because less cross-linking may occur during preparation. Thus, another preferred $R^1$ group is t-butylglycidyl ether.

A preferred flame-retardant use is incorporation into or copolymerization with other structural polymer monomers, especially in polyethers, polyurethanes and polyesters. These are made by known methods such as simply adding to the comonomer or structural material. Preferred methods are taught by Jackson, U.S. Pat. No. 3,402,169 (1968), by Ginter et al., U.S. Pat. No. 4,298,709 (1981) and by Pawloski et al., U.S. Pat. No. 4,365,026 (1982) (each of which is incorporated herein by reference). A most preferred flame-retardant use is in polyurethanes, especially foams and most especially rigid foams.

The compounds of this invention which contain primary hydroxyl groups may be readily reacted with organic polyisocyanate alone or in combination with other reactants used in the fabrication of polyurethane polymers. Persons of ordinary skill in the art are well able to devise suitable formulations for producing polyurethanes according to this invention. Descriptions of the various reactants for such formulations are found in the following publications: *Kirk-Othmer Encyclopedia of Chemical Technology*, "Foamed Plastics", Vol. 9, pp. 853-854 (1966) and Saunders et al., *Polyurethanes, Chemistry and Technology*, Vols. I and II, Interscience Publishers (1963).

The polyurethanes of this invention comprise organic polyisocyanates, polyahls and flame-retarding amounts of the trihalovinyl polyol ethers. Alternatively, trihalovinyl polyol ethers with active hydrogen moiety may be the polyahls polymerized with the organic polyisocyanates to foam polyurethanes.

The term polyahl includes any organic compound having at least two active hydrogen moieties and an average molecular weight of at least 62. For the purpose of this invention, an active hydrogen moiety refers to a moiety containing a hydrogen atom which, because of its position in the molecule, displays significant activity according to the Zerewitnoff test described by Kohler et al in the *J. Am. Chem. Soc.*, 49, 3181-88 (1927). Illustrative of such active hydrogen moieties are —COOH, —OH, NH$_2$, =NH, CONH$_2$, SH and —CONH—. Typical polyahls include polyols, polyamines, polyamides, polymercaptans, polyacids and the like, particularly as exemplified by Rosenkranz et al. in U.S. Pat. No. 3,928,299 (1975) (incorporated herein by reference).

Of the foregoing polyahls, the polyols are preferred. Examples of such polyols useful in this invention are other polyol polyethers, the polyol polyesters, hydroxy functional acrylic polymers, hydroxyl-containing epoxy resins, polyhydroxy terminated polyurethane polymers, polyhydroxyl-containing phosphorus compounds and alkylene oxide adducts of polyhydric thioethers including polythioethers, acetals including polyacetals, aliphatic and aromatic polyols and thiols including polythiols, ammonia and amines including aromatic, aliphatic and heterocyclic amines including polyamines as well as mixtures thereof. Alkylene oxide adducts of compounds which contain two or more different groups within the above-defined classes may also be used such as amino alcohols which contain an amino group and a hydroxyl group. Also alkylene adducts of compounds which contain one —SH group and one —OH group as well as those which contain an amino group and a —SH group may be used.

Any of the trihalovinyl polyol ethers, especially of the formula

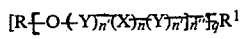

and optionally another polyahl is readily reacted with an organic polyisocyanate to form desired polyurethane products using conventional polyurethane reaction conditions and procedures. Such reaction and procedures are optionally carried out in the presence of chain extending agents, catalysts, surface active agents, stabilizers, blowing agents, fillers and/or pigments. In the preparation of foamed polyurethane, suitable procedures for the preparation of same are disclosed by Hoppe et al. in U.S. Pat. No. Re 24,514 (reissued 1958) (incorporated herein by reference). When water is added as the blowing agent, corresponding quantities of excess isocyanate to react with the water and produce carbon dioxide may be used. It is also possible to proceed with the preparation of the polyurethane plastics by a prepolymer technique wherein an excess of organic polyisocyanate is reacted in a first step with the trihalovinyl polyol ether and optionally another polyahl to prepare a prepolymer having free isocyanate groups which is then reacted in a second step with water to prepare a foam. Alternatively, the components may be reacted in a single working step commonly known as the "one-shot" technique of preparing polyurethanes. Furthermore, instead of water, low boiling hydrocarbons such as pentane, hexane, heptane, pentene, and heptene; azo compounds such as azohexahydrobenzodinitrile; halogenated hydrocarbons such as dichlorodifluoromethane, trichlorofluoromethane, dichlorodifluoroethane, vinylidene chloride and methylene chloride may be used as blowing agents.

The foams may also be prepared by the froth technique as described by Dunlap et al. in U.S. Pat. No. 3,755,212 (1973); by Barron et al. in U.S. Pat. No. 3,821,130 (1974); and by Walters et al. in U.S. Pat. No. 3,849,146 (1974) (each incorporated herein by reference).

Other polyether polyols which are most advantageously employed in the practice of this invention are other polyalkylene polyether polyols including other polymerization products of alkylene oxides and other oxiranes with water or polyhydric alcohols having from two to eight hydroxyl groups. Exemplary alcohols that are advantageously employed in making the polyether polyols (and trihalovinyl polyol ethers) inlcude ethylene glycol; 1,3-propylene glycol, 1,2-propylene glycol, 1,4-butylene glycol, 1,3-butylene glycol, 1,2-butylene glycol, 1,5-pentanediol, 1,7-heptanediol, glycerol, 1,1,1-trimethylolpropane, 1,1,1-trimethylolethane, hexane-1,2,6-triol, α-methyl glucoside, pentaerythritol, erythritol, pentatols and hexatols. Also included within the term "polyhydric alcohol" are sugars such as glucose, sucrose, fructose and maltose as well as compounds derived from phenols such as 2,2-(4,4'-hydroxyphenyl)-propane, commonly known as bisphenol A. Illustrative oxiranes that are advantageously employed in the preparation of the polyether polyols (and trihalovinyl polyol ethers) include simple alkylene oxides such as ethylene oxide, propylene oxide, butylene oxide, and amylene oxide; glycidyl ethers such as t-butyl glycidyl ether and phenyl glycidyl ether; and random or block copolymers of two or more of these oxiranes. The polyalkylene polyether polyols may be prepared from other starting materials such as tetrahydrofuran and alkylene oxide tetrahydrofuran copolymers; epihalohydrins such as epichlorohydrin; as well as aralkylene oxides such as styrene oxide. The polyalkylene polyether polyols may have primary, secondary or tertiary hydroxyl groups and, preferably, are polyethers prepared from alkylene oxides having from two to six carbon atoms such as ethylene oxide, propylene oxide and butylene oxide. The other polyalkylene polyether polyols may be prepared by any known process such as, for example, the process disclosed in *Encyclopedia of Chemical Technology,* 18, 633–45; 19, 249–50, published by Interscience Publishers, Inc. (1982), or by Schmidt et al. in U.S. Pat. No. 1,922,459 (1933) (incorporated herein by reference). Also suitable are other polyether polyols and processes for preparing them that are described in Shick. M. J., *Nonionic Surfactants,* Marcel Dekker, Inc., New York (1967); by Smith in U.S. Pat. No. 2,891,073 (1959); by Pannell in U.S. Pat. No. 3,058,921 (1962); by Baggett et al. in U.S. Pat. No. 2,871,219 (1959); and British Patent No. 898,306 (published 1962) (each incorporated herein by reference) and British Patent No. 898,306. Other polyether polyols which are most preferred include the alkylene oxide addition products of water, trimethylolpropane, glycerine, pentaerythritol, sucrose, sorbitol, propylene glycol and blends thereof having hydroxyl equivalent weights of from about 250 to about 5000.

The trihalovinyl polyol ethers are preferably employed in combination with other polyahls commonly employed in the art. Accordingly, any of the polyahls which are described above for use in the preparation of the polymer dispersions of the present invention may be employed.

Organic polyisocyanates which may be employed include aromatic, aliphatic and cycloaliphatic polyisocyanates and combinations thereof. Representative of these types are the diisocyanates such as m-phenylene diisocyanate, tolylene-2,4-diisocyanate, tolylene-2,6-diisocyanate, hexamethylene-1,6-diisocyanate, tetramethylene-1,4-diisocyanate, cyclohexane-1,4-diisocyanate, hexahydrotolylene diisocyanate (and isomers), naphthylene-1,5-diisocyanate, 1-methoxyphenyl-2,4-diisocyanate, diphenylmethane-4,4-diisocyanate, 4,4'-biphenylene diisocyanate, 3,3'-dimethoxy-4,4'-biphenyl diisocyanate, 3,3'-dimethyl-4,4'-biphenyl diisocyanate, and 3,3'-dimethyldiphenylmethane-4,4'-diisocyanate; the triisocyanates such as 4,4',4'-triphenylmethane triisocyanate, polymethylene polyphenylisocyanate and tolylene-2,4,6-triisocyanate; and the tetraisocyanates such as 4,4'-dimethyldiphenylmethane-2,2',5,5'-tetraisocyanate. Especially useful due to their availability and properties are tolylene diisocyanate, diphenylmethane-4,4'-diisocyanate and polymethylene polyphenylisocyanate.

Crude polyisocyanate may also be used in the practice of the present invention, such as crude toluene diisocyanate obtained by the phosgenation of a mixture of toluene diamines or crude diphenylmethylene diisocyanate obtained by the phosgenation of crude diphenylmethylenediamine. The preferred undistilled or crude isocyantes are disclosed by Kaplan in U.S. Pat. No. 3,215,652 (1965) (incorporated herein by reference).

Chain-extending agents which may be employed in the preparation of the polyurethane compositions of the present invention include those compounds having at least two functional groups bearing active hydrogen atoms such as water, hydrazine, primary and secondary diamines, amino alcohols, amino acids, hydroxy acids, glycols or mixtures thereof. A preferred group of chain-extending agents includes water and primary and secondary aromatic diamines which react more readily with the isocyanate than does water such as phenylenediamine, bis(3-chloro-4-aminophenyl)methane, 2,4-diamino-3,5-diethyl toluene, trisecondary butanolamine, isopropanolamine, diisopropanolamine, N-(2-hydroxypropyl)ethylenediamine, and N,N'-di(2-hydroxypropyl)ethylenediamine.

The urethane reaction of polyisocyanate with the trihalovinyl polyol ethers, especially of the general formula

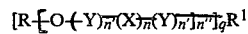

and optionally other polyahls is advantageously carried out in the presence of an amount of a urethane-type catalyst which is effective to catalyze the reaction of the hydroxy group with the polyisocyanate. Preferably, the amount of urethane catalyst is an amount comparable to that used in conventional urethane-type reactions.

Any suitable urethane catalyst may be used including tertiary amines, such as, for example, triethylenediamine, N-methyl morpholine, N-ethyl morpholine, diethyl ethanolamine, N-coco morpholine, 1-methyl-4-dimethylaminoethyl piperazine, 3-methoxy-N-dimethylpropylamine, N,N-dimethyl-N',N'-methyl isopropyl propylene diamine, N,N-diethyl-3-diethylaminopropylamine, dimethyl benzylamine and the like. Other suitable catalysts are, for example, tin compounds such as stannous chloride, tin salts of carboxylic acids such as stannous octate dibutyltin di-2-ethyl hexanoate, as well as other organometallic compounds such as are disclosed by Brochhagen et al. in U.S. Pat. No. 2,846,048 (1958) (incorporated herein by reference).

A wetting agent(s) or surface-active agent(s) is generally necessary for production of high grade polyurethane foam according to the present invention, since in the absence of same, the foams collapse or contain very large uneven cells. Numerous wetting agents have been found satisfactory. Nonionic surfactants and wetting agents are preferred. Of these, the nonionic surface-active agents prepared by the sequential addition of propylene oxide and then ethylene oxide to propylene glycol and the solid or liquid organosilicones have been found particularly desirable. Other surface-active agents which are operative, although not as preferred, include polyethylene glycol ethers of long chain alcohols, tertiary amine or alkylolamine salts of long chain alkyl acid sulfate esters, alkyl sulfonic esters and alkyl arylsulfonic acids.

The trihalovinyl polyol ethers may be employed as adhesives, especially with epoxy-type resins and polythiols. Preferably, the other properties of the composition, especially as related to its flame-retardant capability and thermal stability, are taken into account in these uses. For example, the composition may be used to coat or cement combustible materials, especially in higher heat areas such as in boiler rooms and engine rooms.

SPECIFIC EMBODIMENTS

The following examples further illustrate the invention. The chemicals are reagent grade or higher unless otherwise noted. All percentages are by weight unless otherwise indicated.

Examples 1–3 illustrate preparation of trihalovinyl polyol ethers of the general formula $[R\{O\{Y\}_{\overline{n}}(X\text{-})_{\overline{n}}(Y)_{\overline{n}'}]_{\overline{n}''}]_q R^1$. Examples 4–5 illustrate trihalovinyl polyol ethers such as incorporated with higher polymers.

EXAMPLE 1

A. Preparation of the Trihaloethyenyl Oxirane m-Chloroperoxybenzoic acid (27.4 g, 0.127 mole at 80 percent titre by iodometric titration with dithionite) is added to a solution of 1,1,2-trichloro-1,3-butadiene (20.0 g, 0.127 mole) in 150 ml of methylene chloride under a nitrogen atmosphere. Stirring is maintained, and the solution is brought to reflux for 24 hours. The solution is cooled, and m-chlorobenzoic acid is filtered and washed with 100 ml of methylene chloride. The filtrate is washed and extracted with two 50-ml portions of 10 percent sodium bisulfite and two 100-ml portions of 5 percent sodium hydroxide. This solution of epoxide is then dried over magnesium sulfate, filtered, and the dried solution is rotary evaporated at reduced pressure which removes the methylene chloride. The resulting oil is vacuum distilled (74° C.–76° C. at 12 mm Hg) through a short Vigreaux column to afford 17.5 g of (1,2,2-trichloroethenyl)-1,2-ethylene oxide (0.097 mole) at 98 percent UPC purity (81 percent of theoretical yield).

Corrected boiling point: 190° C. (nomogram method). Anal. Calcd. for: C, 27.70 percent; H, 1.75 percent; Found: C, 27.73 percent; H, 1.74 percent. $^1$H nuclear magnetic resonance (CDCl$_3$) δ: 4.05 (m, 1H), 2.98 (m, 2H). $^{13}$C nuclear magnetic resonance (CDCl$_3$) δ: 128.8 (s), 122.5 (s), 49.6 (d), 46.5 (t). Mass spectra (70 eV): parent manifold 172–176 (4.5–1.3 percent), base peak 109.

B. Preparation of the Trihalovinyl Polyol Ether from the Trihaloethenyl Oxirane

Into a flask are placed 39.3 g (0.15 mole) of 2,2-bis(bromomethyl)-1,3-propanediol and 200 ml of chloroform. This mixture is heated until a solution is obtained. Then, 1 ml of BF$_3$-etherate is added, and a solution of 26.8 g (0.15 mole) of 1,2,2-trichloroethenyl)oxirane and 6.6 g (0.15 mole) of ethylene oxide in 50 ml of chloroform is added dropwise. The mixture is then stirred until reaction is complete. Some 5 percent NaOH is added, and the mixture is stirred. The product phase is separated, dried over sodium sulfate, filtered, and the solvent is removed to give 62 g of oil with Brookfield viscosity of 12,000 cps at 25° C. (number 6 spindle; 100 rpm). The yield of trihalovinyl polyol ether is 86 percent of theoretical.

EXAMPLE 2

Into a flask are placed 7.9 g (0.03 mole) of 2,2-bis(bromomethyl)-1,3-propanediol and 150 ml of methylene chloride. This mixture is stirred and heated to reflux. The heat source is removed, and 0.5 ml of BF$_3$-etherate is added. This addition is followed by the dropwise addition of 3.9 g (0.03 mole) of t-butyl glycidyl ether. The mixture is stirred until reaction is complete. More BF$_3$-etherate catalyst (0.5 ml) is added, and 78 g (0.45 mole) of (1,2,2-trichloroethenyl)-1,2-ethylene oxide is then added dropwise. After this addition, 0.5 ml more catalyst is added, and the mixture is stirred at reflux until reaction is complete. The flask is equipped with a short distillation column, and 1.0 g of 85 percent phosphoric acid is added. The mixture is slowly heated to 115° C. while low boilers distilled off. The 115° C. temperature is maintained until reaction is complete as nuclear magnetic resonance spectra indicates. After cooling, the product is taken up in 200 ml of methylene chloride and is stirred with 100 ml of dilute (5 percent (aqueous)) sodium hydroxide. The product layer is separated, dried over sodium sulfate, filtered, and the solvent is removed by distillation under reduced pressure to give 79 g of oil with Brookfield viscosity of 196,000 cps at 25° C. (number 6 spindle; 100 rpm). The yield of trihalovinyl polyether is 90 percent of theoretical.

EXAMPLE 3

Using the procedure of Example 2, 13.1 g (0.05 mole) of 2,2-bis(bromomethyl)-1,3-propanediol, 250 ml of methylene chloride and 6.5 g (0.05 mole) of t-butyl glycidyl ether are stirred and refluxed. The heat source is removed and 1.0 ml of BF$_3$-etherate is added. This addition is followed by dropwise addition of a solution of 34.7 g (0.2 mole) of (1,2,3-trichloroethenyl)ethylene oxide/5.8 g (0.1 mole) of propylene oxide/69.4 g (0.75 mole) of epichlorohydrin. After this addition, 2.0 ml more of BF$_3$-etherate is added and the mixture is stirred and refluxed until reaction is complete. A short distillation column is added. Phosphoric acid (85 percent) is added and the mixture is slowly heated to 120° C. while the low boilers are distilled off. The product is taken up in methylene chloride and is then stirred with dilute sodium hydroxide. The product layer is dried and distilled under vacuum to give 122 g of oil with a Brookfield viscosity of 4,500 cps at 25° C. (number 6 spindle; 100 rpm). The yield of trihalovinyl polyether is 96 percent of theoretical.

EXAMPLE 4

A flexible polyurethane foam is prepared as follows.

The A-side (i.e., isocyanate side) of the formulation is weighed out. The A-side is 110 g of toluene diisocyanate.

The B-side (i.e., polyol side) of the formulation is weighed out as follows: 100 g of polyol with a molecular weight of about 3,000 and hydroxyl number of about 53.4 (Voranol ® 3137, trademark of The Dow Chemical Company), 10 g of trihalovinyl polyol ether of Example 1, 5 g of deionized water, 6 g of methylene chloride, 1 g of silicone surfactant (Q2-5125 ®, trademark of Dow Corning Corp., Midland, MI), 0.2 g of amine catalyst (NIAX ™ A-1, available from Union Carbide) and 0.3 g of stannous octoate catalyst (T-10, available from M&T Chemical Co.).

The B-side components are combined and mixed at 1,000 rpm (i.e., rotations per minute of the stirrer) for 10 seconds. The A-side is quickly added, and the A-B mixture is mixed at 1,000 rpm for 5 seconds and poured into an 8-inch cylindrical paper container prior to creaming. After creaming, the foam is immediately placed in an oven at 95° C. for 20 minutes to cure.

If the foam is subjected to the testing method of the California Vertical Burn test, it passes the requirements. The foam shows little or no scorch.

EXAMPLE 5

A rigid polyurethane foam is prepared as follows.

The A-side (i.e., isocyanate side) of the formulation is weighed out. The A-side is 105 g of 4,4'-diphenylmethane diisocyanate (Mondur ® MR, available from Mobay).

The B-side (i.e., polyol side) of the formulation is weighed out as follows: 80 g of polyol with hydroxyl number of about 320 (Voranol ® 456/640—a 50/50 blend—The Dow Chemical Company), 20 g of trihalovinyl polyol ether of Example 1, 5 g of deionized water, 38 g of $CCl_3F$ (Freon ® 11, E. I. duPont de Nemours & Co., Wilmington, DE), 1 g of silicone surfactant (Q2-5125 ®, Dow Corning Corp., Midland, MI), 1 g of dimethylcyclohexylamine (Polycat ® 8 amine catalyst, Abbot Labs, Chicago, IL) and 0.2 g of stannous octoate catalyst (T-131, M&T Chemical Co., Woodbridge Ave., Rahway, NJ).

The B-side components are combined and mixed at 1,000 rpm (i.e., rotations per minute of the stirrer) for 10 seconds. The A-side is quickly added, and the A-B mixture is mixed at 1,000 rpm for 5 seconds and poured into an 8-inch cylindrical paper container prior to creaming. The cream time is 10 seconds. After creaming, the foam is is allowed to age for two days (48 hours).

If the foam is subjected to the following vertical burn testing method, it passes the requirements. The foam may have little or no scorch.

The vertical burn test involves ignition of a sample of the foam ⅞"×3"×¼" (i.e., 2.22 cm×7.62 cm×0.635 cm) in a 25 percent by weight $O_2$ atmosphere and measurement of the time required for the foam to burn 2 inches (i.e., 5.08 cm). The burn rate is then calculated in inches (cm) per minute. It is believed that a vertical burn rate of less than 10 inches (i.e., 25.4 cm) per minute for a rigid polyurethane foam would enable the foam to pass the Class II flame spread requirement (i.e., 75 F.S. or less) for the ASTM E-84 Steiner (i.e., 25-foot) tunnel test.

We claim:

1. A trihalovinyl polyol ether.
2. The composition of claim 1 having a limiting oxygen index of above 21 as measured by the oxygen demand test.
3. The composition of claim 2 having a scorch resistance ΔE value by the Gardner Colorimeter test of 6.0 or below.
4. The composition of claim 3 wherein the scorch resistance ΔE value by the Gardner Colorimeter test is 4.0 or below.
5. The composition of claim 2 wherein the limiting oxygen index is 25 or above.
6. The composition of claim 5 wherein the limiting oxygen index is 30 or above.
7. The composition of claim 3 wherein the limiting oxygen index is 25 or above.
8. The composition of claim 7 wherein repeating units of a urethane are present.
9. The composition of claim 8 wherein the trihalovinyl polyol ether before incorporation into the polyurethane has a Brookfield viscosity of about 200,000 cps or less.
10. The composition of claim 9 wherein the polyurethane is a rigid foam which passes the Class II flame spread requirements of ASTM E-84.
11. The composition of claim 9 wherein the viscosity is about 20,000 or less.
12. The composition of claim 11 wherein the viscosity is about 5,000 or less.
13. The composition of claim 12 wherein the polyurethane is a flexible foam and the limiting oxygen index is measured by passing the California Vertical burn test.
14. The composition of claim 1 wherein the trihalovinyl polyol ether is of the general formula:

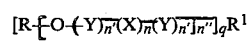

wherein

R is independently at each occurrence hydrogen, $C_{1-20}$ hydrocarbyl, $C_{1-20}$ halocarbyl, $C_{1-20}$ halogenated hydrocarbyl, $C_{1-20}$ hydroxylated hydrocarbyl, $C_{1-20}$ hydroxylated hydrocarbyl, or $C_{1-20}$ halogenated-hydroxylated hydrocarbyl, each of which may additionally contain other ether functionality and $C_{1-20}$ attached organic or attached inorganic moiety;

$R^1$ is independently at each occurrence hydrogen, $C_{1-20}$ attached organic or attached inorganic moiety;

X is independently at each occurrence 1-(1,2,2-trihaloethenyl)-1,2,2-tri-substituted ethoxy;

Y is independently at each occurrence 1,1,2,2-tetrasubstituted ethoxy;

n is independently at each occurrence an integer from one to about 20;

n' is independently at each occurrence an integer from zero to about 20;

n" is independently at each occurrence an integer from one to about 20; and q is independently at each occurrence an integer from one to three.

15. The composition of claim 14 wherein the halogen of X is bromine or chlorine.

16. The composition of claim 15 wherein the halogen of R and Y is bromine or chlorine.

17. The composition of claim 16 wherein $R^1$ is a dealkylatable hydrocarbon moiety.

18. The composition of claim 16 wherein the halogen of X is chlorine.

19. The composition of claim 18 having a viscosity of about 200,000 cps or below.

20. The composition of claim 19 having a viscosity of about 20,000 cps or below.

21. The composition of claim 20 having a viscosity of about 5,000 cps or below.

22. A composition of matter comprising a polyahl and at least one trihalovinyl polyol ether.

* * * * *